United States Patent [19]

Jumashev et al.

[11] 4,059,115

[45] Nov. 22, 1977

[54] SURGICAL INSTRUMENT FOR OPERATION OF ANTERIOR FENESTRATED SPONDYLODESSIS IN VERTEBRAL OSTEOCHONDROSIS

[76] Inventors: Georgy Stepanovich Jumashev, Kutuzovsky prospekt. 21/1, kv. 86; Motel Khaimovich Furman, ulitsa Svobody, 93, kv. 393, both of Moscow, U.S.S.R.

[21] Appl. No.: 695,407

[22] Filed: June 14, 1976

[51] Int. Cl.$^2$ .................. A61B 17/14; A61B 17/16
[52] U.S. Cl. .................. 128/317; 128/310; 408/36; 408/703
[58] Field of Search .................. 128/305, 305.1, 310, 128/317, 69; 408/36, 54, 67, 204, 206, 224, 703

[56] References Cited

U.S. PATENT DOCUMENTS

| | | | |
|---|---|---|---|
| 651,921 | 6/1900 | De Vilbiss | 128/310 |
| 847,133 | 3/1907 | Velasco | 128/310 |
| 2,573,462 | 10/1951 | Lindsey | 408/204 X |
| 2,896,729 | 7/1959 | Brechlin | 408/224 X |
| 3,848,601 | 11/1974 | Ma et al. | 128/305 |

Primary Examiner—Channing L. Pace
Attorney, Agent, or Firm—Steinberg & Blake

[57] ABSTRACT

A surgical instrument for the surgical operation of anterior fenestrated spondylodesis comprising an elongated hollow body with a handle at one end, and a detachable hollow cylindrical cutter with a cutting edge, at the other. Incorporated within the body is a shaft with a knife on the end situated within the cavity of the cutter. The instrument has a device for securing the shaft in the body in a position whereat the blades and cutting edge of the knife and the cutter lie in the same plane. The cutter is intended for excising two transplants in the shape of cylindrical segments from two adjacent vertebrae, and the knife, for undercutting then, once they are formed by the cutter. Also situated in the cutter's cavity is a limit flange secured on the shaft, which comes in contact with the surface of the vertebral bodies and restricts the depth to which the knife descends into the intervertebral slit and, together with a stop on the proximal end of the body interacting with the end of the shaft, ensures the right depth of the cutter's penetration into the adjacent vertebral bodies.

The instrument is reliable, does not endanger, during surgery, nearby large vessels and nerve formations, and precludes the penetration of the knife into the vertebral canal. The instrument permits the operation to be performed on any region of the spinal column.

7 Claims, 23 Drawing Figures

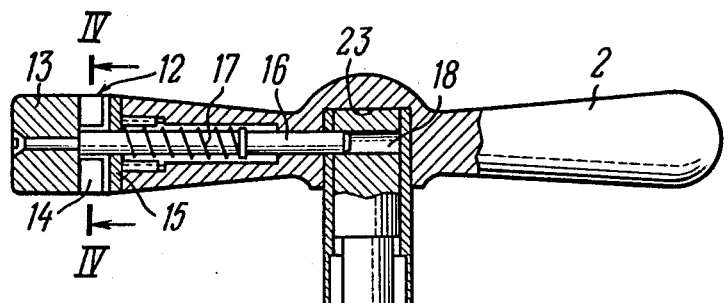
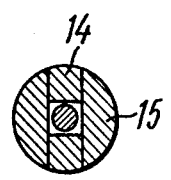
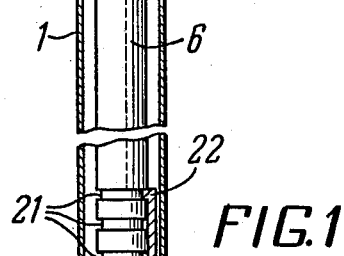
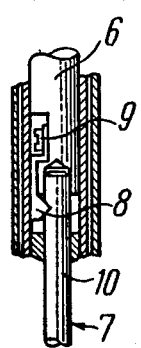
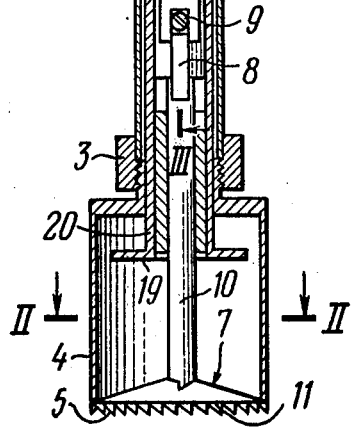
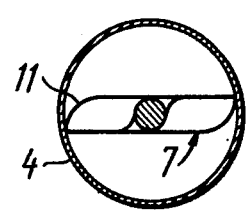

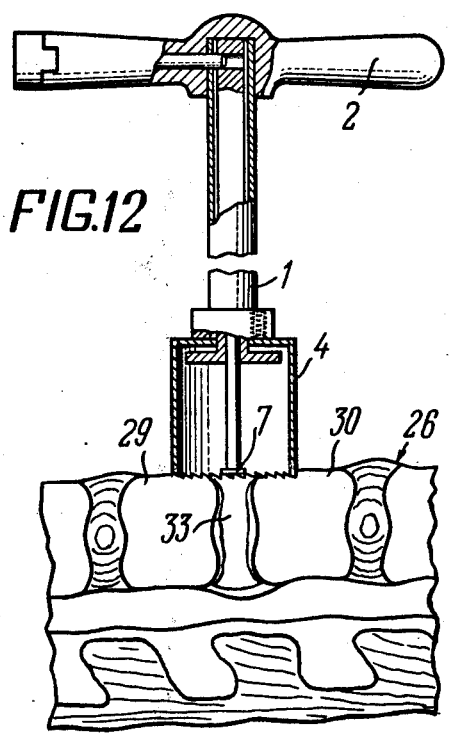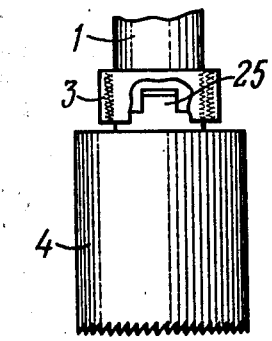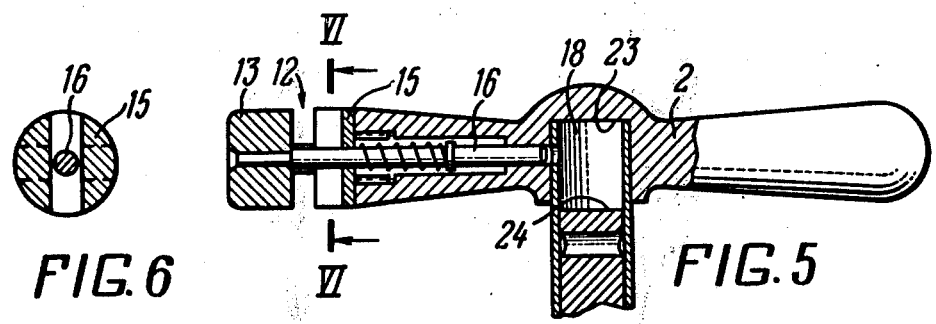

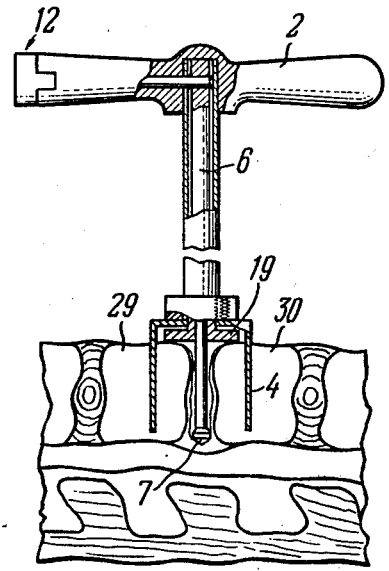
FIG.15
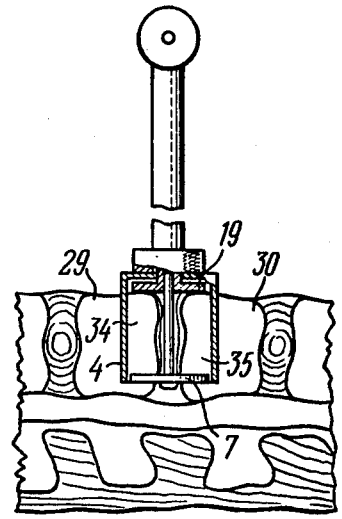
FIG.16
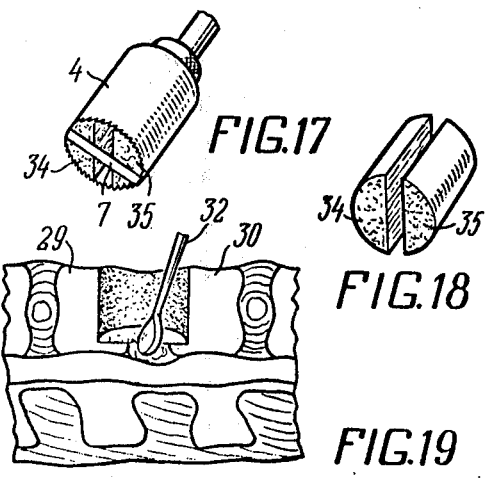
FIG.17
FIG.18
FIG.19

SURGICAL INSTRUMENT FOR OPERATION OF ANTERIOR FENESTRATED SPONDYLODESSIS IN VERTEBRAL OSTEOCHONDROSIS

This invention relates to medicine, and more particularly to orthopedics and traumatology, and is concerned with the design of an instrument for the surgical operation of anterior fenestrated spondylodesis, used for the treatment of vertebral osteochondrosis.

Vertebral osteochondrosis is a rather widespread disease, standing out as one of the primary causes of disability and temporary incapacity. Grave forms of osteochondrosis which do not respond to conservative therapy are treated by surgery.

Surgery for the removal of a diskal hernia by laminectomy is frequently accompanied by residual pain and relapses. The main causes of these reverses are continuing degeneration and protrusion of the remaining parts of the disk (whose complete is impossible by the posterior approach), progressive diminution of the height of the affected disk, which does not, however, reach the stage of fusion of the vertebrae, i.e. of an osseous block, which leads to the compression of nervous roots, obstruction of blood circulation in the vertebral canal and a painful (pathological) mobility between the vertebrae, of the deforming arthrosis type; thus damaging the posterior matrix, both osseous and muscular, of the spinal column, and resulting in its deformation and instability.

The most radical and pathogenetically sound surgical operation for vertebral osteochondrosis, rather than mere removal of a diskal hernia, is a total diskectomy and spondylodesis between the vertebral bodies without reducing the height between the vertebral bodies due to the use of a bone transplant. Such surgery can be performed only through the anterior approach. The positive results of such operations proved much better, and more important still, more stable. Surgery per se, however, has involved some negative moments. Thus, in order to form the slot intended for the introduction of the transplant, a hammer and chisel were used, which caused concussion from the blows, a hazard not only to the nearby large vessels, but to elements of the vertebral canal as well. Additional injury was inflicted when a bone transplant was removed from another part of the body, for example, from the tibia or the iliac bone. Nor was it possible to effect an accurate fit of the transplant to the bed, which prolonged the subsequent process of ankylosis, i.e. fusion. Diskal herniotomy through the anterior approach was further made difficult because of the narrowness of the bed; the surgical operation itself was also protracted.

Still another and more progressive method known in the art of surgical treatment of vertebral osteochondrosis is anterior fenestrated spondylodes is and a surgical instrument for its performance.

The operation of anterior fenestrated spondylodesis rests on the following principle. The anterior surfaces of the vertebrae and disks to be operated upon are exposed through an anterior approach. Upon the removal of the affected disk (diskectomy) two transplants are formed by means of the aforementioned instrument in the shape of cylindrical segments from the bodies of two adjacent vertebrae, with the flat lateral sides of the transplants being parallel to the intervertebral slit. Then the transplants are rotated through 90°, thereby closing in the intervertebral slit, with an autoplastic cortical transplant placed between the autoplastic transplants, serving as a spacer and also stimulating osteogenesis.

The prior art surgical instrument for the operation of anterior fenestrated spondylodesis is essentially a hollow elongated cylindrical cutter with a cutting edge intended for simultaneous excision of transplants out of two adjacent vertebrae, and a shaft situated within the cutter coaxially therewith, with a knife being secured on its end for introduction into the intervertebral slit and effecting, through its rotation, the undercutting of the transplants after their excision by the cutter. The instrument has two detachable handles: one connected with the cutter and ensuring the rotation thereof, and the other secured on the shaft and ensuring the rotation of the knife. A limit ring is secured by means of two stop screws outside the cutter for restricting the depth of the latter's penetration into the vertebral bodies and intended for coming in contact with the vertebral bodies and limiting the depth of the cutter's penetration thereinto.

The formation of two transplants in the shape of cylindrical segments by this prior art instrument is practically divided into two stages, the first of which is the excision of the cylindrical surfaces of the transplants. For this purpose, the cutter, with the shaft and knife removed, is set against the two adjacent vertebrae with the affected disk already removed from between them, and by rotating the detachable handle connected with the cutter, the latter is introduced into the bodies of these vertebrae. The depth of the cutter's penetration is controlled by the external limit ring fixed at a preset distance from the cutter's cutting edge. The second stage is the undercutting of the transplants. For this purpose, the detectable handle is removed and the shaft with the knife and handle is inserted into the cutter. In doing so, the knife is lowered into the intervertebral slit to the level of the cutter's cutting edge, which corresponds to a mark on the upper part of the shaft. The shaft is secured by means of a securing device. The transplants are undercut by rotating the shaft with the knife by means of the handle set on the shaft.

This prior art instrument allows successful performance of the operation of anterior fenestrated spondylodesis. However, the design of this instrument has a number of disadvantages. Thus, the external limit ring secured by two screws, obstructs the surgeon's field of vision as it occupies an extra area, and, when the cutter rotates, endangers the nearby large vessels and nerves. The replacement of two handles (for the cutter and knife) during the operation prolongs the latter. There is no foolproof guarantee against injury to the vertebral canal by the knife before the shaft with the knife is secured by the securing device. The instrument is designed for operating upon some one region of the spinal column only, in accordance with the respective dimensions of the particular cutter and knife.

It is an object of the present invention to provide a surgical instrument for the operation of anterior fenestrated spondylodesis in vertebral osteochondrosis that will not endanger the nearby large vessels and nerve formations during rotating movements when excising transplants.

It is another object of the invention to provide an instrument that will completely rule out the possibility of the knife for undercutting the transplants penetrating the vertebral canal.

Still another object of the invention is to reduce the time required for surgery.

A further object of the invention is to provide a universal instrument that will make it possible to operate upon any region of the spinal column (cervical, thoracic and lumbar).

It is still another object of the invention to enlarge the operational observation field through reducing excessive parts of the instrument.

These and other objects are achieved in that an instrument is proposed for the surgical operation of anterior fenestrated spondylodesis in vertebral osteochondrosis which, in accordance with the invention, comprises a hollow elongated cylindrical body with a handle secured transversally thereto at its proximal end, and a detachable hollow cylindrical cutter with a cutting edge, secured coaxially therewith on the distal end of the body and intended for the simultaneous excision of two transplants in the shape of cylindrical segments from the bodies of two adjacent vertebrae. Situated in the body coaxially therewith is a freely rotatable and longitudinally movable shaft, on whose end is secured a detachable knife situated within the cavity of the cutter. The knife's blades lie in a plane parallel to that of the cutting edge of the cutter, and the size of the knife is so selected as to enable its introduction into the intervertebral slit following the removal of the intervertebral disk and complete undercutting of said transplants following their excision by the cutter, by subsequent rotation of the knife. The instrument also contains a device for securing the shaft relative to the body in a position whereat the cutting edge and the blades of the cutter and the knife lie in the same plane, and preventing, at the same time, the shaft's rotation relative to the body, a limit flange fastened on the shaft and situated in the inner cavity of the cutter at a distance from the blades of the knife, equal to the required height of the transplants being excised, and intended for coming in contact with the surface of the bodies of said adjacent vertebrae and thereby limiting the depth to which the knife is lowered into the intervertebral slit, and a stop situated on the proximal end of the body interacting with the end of the shaft during the latter's longitudinal movement towards the proximal end of the body and thereby ensuring, together with the limit flange, the preset depth of cutter penetration into the bodies of adjacent vertebrae.

A limit flange allowing the cylindrical cutter to penetrate into the bodies of adjacent vertebrae to a definite depth and preventing the shaft with the knife from descending below the cutting edge of the cutter, makes it possible to do away with the external limit ring with two screws. As a result, the danger of injuring nearby large vessels and nerve formations, and of the penetration of the cutter of the knife into the vertebral canal is removed. The observation field of the surgical wound and of the anterior surface area of the spinal column is at the same time increased. The new instrument has but one handle fitted with a securing device for securing the shaft with the knife relative to the body, which allows to combine two processes: the excision of the transplants and their severing from the spinal column. The time of the operation is thereby reduced. The cutter and knife are detachable and available in sets of different sizes, so that the same instrument complete with a set of cutters and knives can be used for surgery on any region of the spinal column (servical, thoracic and lumbar).

It is preferable that the limit flange be secured on the shaft so that its distance from the blades of the knife is adjustable, thereby allowing to control the height of the transplants being excised.

The limit flange can be carried by a sleeve set on the shaft, rotatably and longitudinally movable therealong, and has a lug engaging with one of a number of annular grooves made on the shaft at some distance one from another, thus permitting adjustment of the distance between the limit flange and the blades of the knife.

It is preferable to so arrange the device securing the shaft relative to the body as to ensure that, in the secured position, the knife secured on the shaft and the handle secured on the body are in the same longitudinal plane, which allows the surgeon during surgery to see the position of the knife by that of the handle.

The proposed instrument has been used for performing the operation of anterior fenestrated spondylodesis in 283 patients with grave forms of vertebral osteochondrosis, 98 of them in the cervical region, 6 in the thoracic and 179 in the lumbar region. All the aforementioned advantages of the instrument were confirmed in practice. During surgery, there were no complications associated with the use of the instrument. Good follow-up results were ascertained in 85 percent of the patients.

The invention will now be described in greater detail with reference to preferred embodiments thereof, taken in conjunction with the accompanying drawings, wherein:

FIG. 1 is a longitudinal section view of a surgical instrument for the operation of anterior fenestrated spondylodesis in vertebral osteochondrosis, in accordance with the invention;

FIG. 2 is a section view along line II—II of FIG. 1;

FIG. 3 is a section view along line III—III of FIG. 1;

FIG. 4 is a section view along line IV—IV of FIG. 1;

FIG. 5 is a longitudinal section view of the instrument's handle with the shaft's securing device in the position with the shaft released, in accordance with the invention;

FIG. 6 is a section view along the line VI—VI of FIG. 5;

FIG. 7 is a partially cut away view of the cutter, in accordance with the invention;

FIGS. 8 to 22 show consecutive steps of the operation of diskectomy with anterior fenestrated spondylodesis performed with the aid of an instrument embodied in accordance with the invention;

Figure 9:
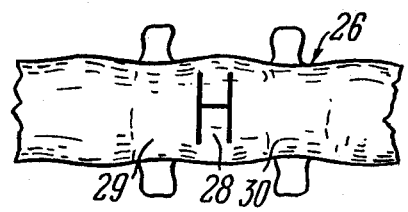

The surgical instrument for the operation of anterior fenestrated spondylodesis in vertebral osteochondrosis comprises a hollow elongated cylindrical body 1 (FIG. 1) with a handle 2 rigidly secured transversely thereto on the proximal end of the body 1. Detachably secured on the distal end of the body 1 by means of a union nut 3 is a hollow cylindrical cutter 4 with a cutting edge 5, intended for simultaneous excision of two transplants in the shape of cylindrical segments from the bodies of two adjacent vertebrae. Situated in the body 1 and coaxially thereto is a shaft 6 with a knife 7 secured on its end (FIGS. 1 and 2). The knife 7 is secured by means of a spring plate 8 (FIGS. 1 and 3), fastened by a screw 9 to the shaft 6, its lug entering a respective depression on the shank 10 of the knife 7. The knife 7, however, may be secured on the shaft 6 also by means of a thread (not shown).

The blades 11 (FIGS. 1 and 2) of the knife 7 lie in a plane parallel to that in which the cutting edge 5 of the cutter 4 is situated.

The size of the knife 7 is so selected that it can be introduced into the intervertebral slit after the removal of the intervertebral disk and provides, upon its subsequent rotation, for complete undercutting of the transplants once they are excised by the cutter 4.

The shaft 6 is freely rotatable and longitudinally movable relative to the body 1. In a position of the shaft 6, whereat the cutting edge 5 of the cutter 4 and the blades 11 of the knife 7 lie approximately in the same plane, the shaft 6 may be secured by means of the securing device 12, which at the same time prevents the rotation of the shaft 6 in the body 1. The securing device 12 has a head 13 with lugs 14 (FIGS. 1 and 4), entering a corresponding slot on a stop bush 15, fastened on the handle 2 (FIG. 1). Rigidly secured on the head 13 is a rod 16 loaded by a spring 17 retained by the stop bush 15. With the shaft 6 in the secured position, the rod 16 enters a hole 18 in the shaft 6. To release the shaft 6, the head 13 is drawn away from the stop bush 15 and turned so that the lugs 14 of the head 13 are withdrawn from the slot in the stop bush 15, as shown in FIGS. 5 and 6, and brought to rest against the striking face of the stop bush 15. Thereupon, the rod 16 is withdrawn from the hole 18 of the shaft 6. The arrangement of the securing device 12 on the handle 2 is such that with the shaft 6 secured the knife 7 (FIG. 1) and the handle 2 are secured in the same longitudinal plane, so that during surgery the surgeon will know the direction of the knife 7 by viewing the handle 2. For preventing the cutter 4 and the knife 7 from penetrating the vertebral canal, the instrument is fitted wth a limit flange 19 situated inside the cutter 4 at a distance from the blades 11 of the knife 7 equal to the required height of the transplants being excised. The limit flange 19 is made on a sleeve 20 set on the shaft 6 movably along the shaft 6 and is rotatable thereon. Three grooves 21 are made on the shaft 6 at some distance one from another for securing the sleeve 20 whose lug 22 can engage with each of them. Each of the grooves 21 has a slightly varying width so that the lug 22 goes easily into a wider part of a groove 21, and, upon the rotation of the sleeve 20, gets wedged in a narrower part of the groove 21, thereby fastening the sleeve 20 on the shaft 6.

The limit flange 19 is intended to in contact with the surface of the bodies of two adjacent vertebrae, thereby limiting the depth to which the knife 7 can be inserted into the intervertebral slit. By selecting a particular groove 21 it is possible to control the distance between the limit flange 19 and the blades 11 of the knife 7, to ensure the necessary height of the transplants being excised.

There is a stop 23 at the proximal end of the body 1 interacting with the end 24 (FIG. 5) of the shaft 6 during the latter's longitudinal movement towards the proximal end of the body 1. Jointly with the limit flange 19, the stop 23 (FIG. 1) ensures the present depth of introduction of the cutter 4 into the bodies of the adjacent vertebrae.

The instrument is supplied with a set of cutters 4, knives 7 and limit flanges 19 to enable the performance of surgery on different regions of the spinal column: cervical, thoracic and lumbar.

Lugs 25 (FIG. 7) on the cutter 4, entering corresponding slots on the body 1, serve to prevent rotation of the cutter 4 relative to the body 1.

For the sterilisation of the instrument its working parts, namely, the cutter, knife, limit flange and shaft, are removed.

Before surgery, the size of the vertebrae to be operated upon is determined by X-ray pictures (direct and lateral), and the cutter 4, limit flange 19 (FIG. 1) and knife 7 of appropriate size are picked from the set.

The sequence of the intrument's assembly is as follows:

1. Securing the limit flange 19 on the shaft 6. For this purpose, the lug 22 of the sleeve 20 of the limit flange 19 is inserted in a groove 21, and by rotating the limit flange 19 through 90° it is secured on the shaft 6. Naturally, for the deep penetration of the cutter 4, that is, for obtaining a large transplant, the limit flange is engaged with the upper groove 21, and vice versa.

2. Securing the knife 7 on the shaft 6. This is effected by inserting the shank 10 of the knife 7 into a bore of the shaft 6 as far as it goes, at which point the spring plate 8 secures it to the shaft 6. 3. Mounting the cutter 4. For this the lugs 25 (FIG. 7) of the cutter 4 are placed in the slots of the body 1 and the connection is made rigid by means of the union nut 3.

4. Securing the shaft 6 (FIG. 1). The latter, in assembled with the limit flange 19 and the knife 7, is inserted into the body 1 to the stop 23. The knife 7 is set parallel to the handle 2, while the shaft 6 is secured in position by the securing device 12.

The operation of diskectomy with anterior fenestrated spondylodesis is carried out with the aid of the proposed instrument in the following manner.

Figure 10:
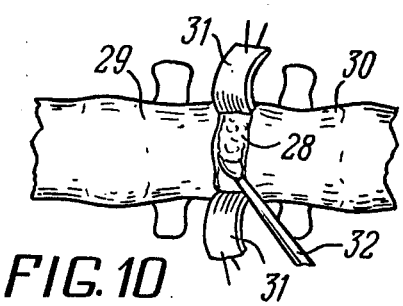
Figure 8:
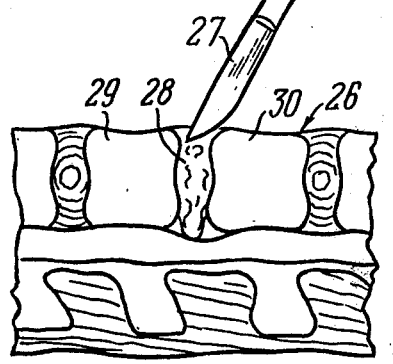

The anterior surface of the spinal column 26 (FIG. 8) is exposed, and an H-like incision of the affected disk 28 (FIGS. 9 and 10) is made with a scalpel 27, i.e. two parallel incisions are made at the borders of the disk 28 with the bodies of the adjacent vertebrae 29 and 30 and one incision connecting them.

Figure 11:
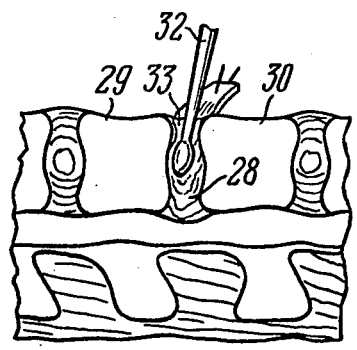

Two flaps 31 (FIG. 10) are formed from the outer layers of the fibrous ring. The flaps 31 are pulled apart on both sides with sutures. The degenerated disk 28 is scraped out with a scalpel and the scoop 32, which leaves in its place a narrow opening, the intervertebral slit 33 (FIG. 11).

The assembled instrument is rested perpendicularly on the spinal column 26 (FIG. 12) over the intervertebral slit 33, so that it covers equal areas of the adjacent vertebral bodies 29 and 30. The handle 2 and the knife 7 are situated parallel to the intervertebral slit 33 (FIG. 12 and subsequent Figures conditionally depict the handle 2 as rotated through 90° for clearer presentation).

Figure 13:
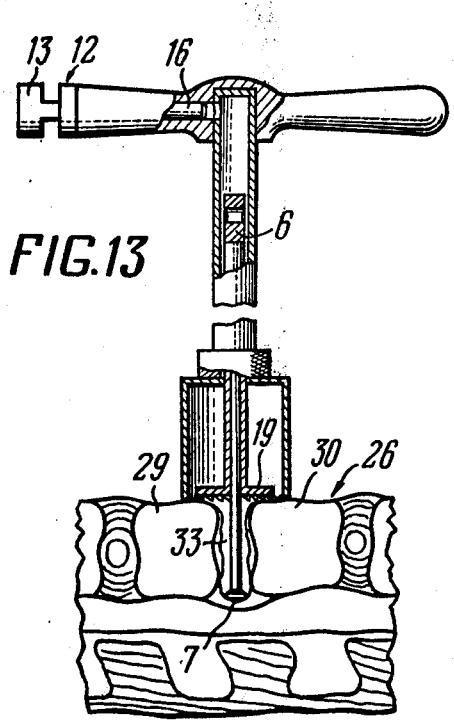

The shaft 6 is released (FIG. 13). For this purpose, the head 13 of the securing device 12 is pulled so that the rod 16 releases the shaft 6. This permits the knife 7, secured on the shaft 6, to drop into the intervertebral slit 33 until the limit flange 19 stops against the anterior surface of the adjacent vertebral bodies 29 and 30. This contact lasts till the end of the instruments's performance. The knife 7, suspended at the level determined by the limit flange 19, remains passive till subsequent securing of the shaft 6.

Figure 14:
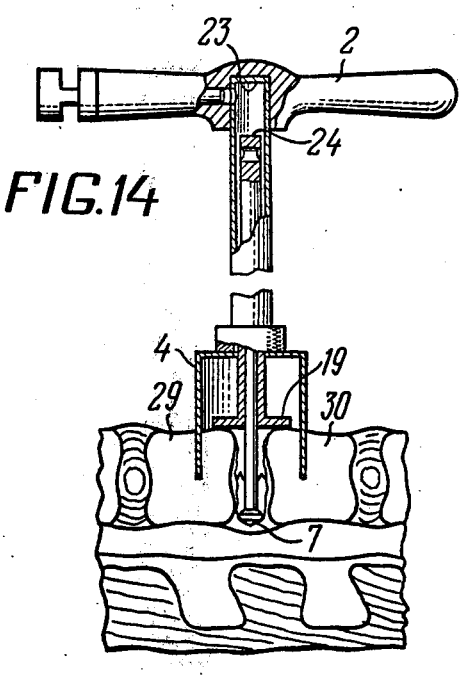

By light rotating movements of the handle 2 accompanied by slight pressure the cutter 4 (FIG. 14) is worked into the bodies of the adjacent vertebrae 29 and 30. In the process of this penetration, the distance between the stop 23 and the upper end 24 of the shaft 6 diminishes. The advance of the cutter 4 ceases altogether at the moment when the stop 23 touches the upper end 24 of the shaft 6 (FIG. 15) and from then on any pressure is conveyed to the limit flange 19 only. At this point, the surgeon clearly feels that further depression of the cutter 4 is obstructed.

The shaft 6 is secured in position with the securing device 12, and the knife 7 is set in the working position, whereby it is linked with the handle 2. By a single rotation of the handle 2 through 180° the transplants 34 and 35 (FIG. 16), excised by the cutter 4, are undercut from their base by the knife 7.

An additional turn of the handle 2 through another 90° will retain the transplants 34 and 35 by means of the knife 7 within the cutter 4, and the instrument, together with the transplants 34 and 35, as shown in FIG. 17, is withdrawn from the wound.

The obtained autoplastic transplants 34 and 35 in the shape of cylindrical segments (FIG. 18) are taken out of the instrument after releasing the shaft 6 (not shown).

The subsequent steps of the operation are the concluding ones and are carried out now without the instrument.

Figure 20:
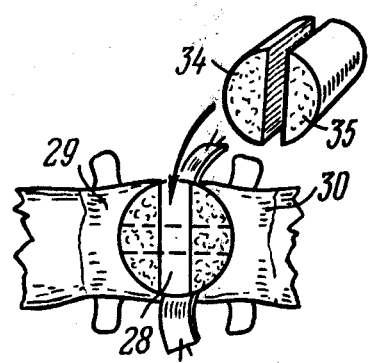
Figure 22:
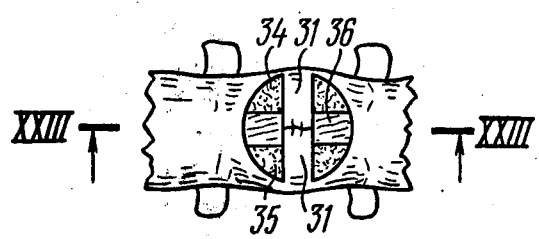
Figure 21:
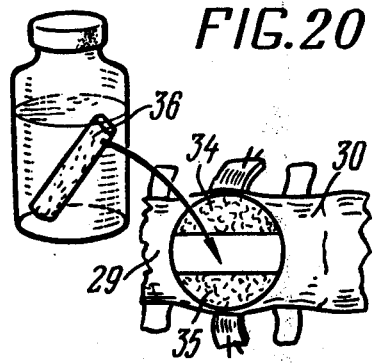

Well visible through the circular bed formed by the removal of the transplants 34 and 35 are the posterior portions of the disk, including the hernial protrusions (FIG. 19), which can be now easily removed with the scoop 32. After additional treatment (clearing from soft tissues) the semicular autoplastic transplants 34 and 35 (FIG. 20), turned through 90° relative to their former position in the vertebrae 29 and 30, are introduced once again into the formed circular bed so that the slit formed between the transplants 34 and 35 is perpendicular to the intervertebral slit 28. A homoplastic cortical transplant 36 (FIG. 21) is tightly packed as a spacer between the transplants 34 and 35, thereby achieving an ideal adaptation between the transplants 34 and 35 and the bodies of the adjacent vertebrae 29 and 30. The flaps 31 (FIG. 22) of the fibrous ring are sutured up like a strap over the transplants 34, 35 and 36.

Figure 23:
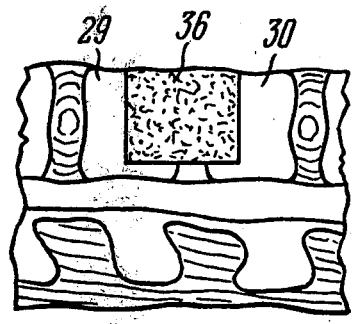
FIG. 23 is a section view along line XXIII—XXIII of FIG. 22.

FIG. 23 shows the depth of penetration of the homoplastic transplant 36, which corresponds to the depth of penetration of the transplants 34 and 35 towards the end of the operation, and not visible in FIG. 23.

The wound is sutured up in a conventional way.

What is claimed is:

1. A surgical instrument for the operation of anterior fenestral spondylodesis in vertebral osteochondrosis, comprising: a hollow elongated cylindrical body; a hollow cylindrical cutter, having a cavity and a cutting edge in a given plane, secured on a distal end of said body coaxially therewith and intended for the simultaneous exicision of two transplants in the shape of cylindrical segments from two adjacent vertebrae separated by an intervertebral slit; a shaft situated in said body coaxially therewith and freely rotatable therein and movable longitudinally with respect thereto; a knife situated in the cavity of said cutter and secured on said shaft for movement jointly therewith, said knife having blades situated in a plane parallel to said given plane, and said blades having a size small enough for introduction of the knife into the intervertebral slit following the removal of an intervertebral disk, said knife being adapted completely to undercut said transplants, after their excision by said cutter, upon subsequent rotation of the knife; a device for securing said shaft relative to the aforementioned body in a position where the cutting edge of the cutter and the blades of the knife lie in approximately the same plane, while preventing the shaft's rotation relative to the body; a limit flange, secured on said shaft and situated within the cavity of said cutter at a distance from the blades of said knife, equal to a predetermined height of the transplants being excised and intended for coming in contact with the surface of said adjacent vertebrae and thereby restricting the depth of the knife's descent into the intervertebral slit; a stop situated at the proximal end of said body, interacting with a proximal end of said shaft during its longitudinal movement towards the proximal end of the body and ensuring thereby, together with said limit flange, a present depth of penetration of the cutter into adjacent vertebrae.

2. A surgical instrument as claimed in claim 1, in which said limit flange is secured on said shaft so as to enable the adjustment of its distance from the blades of the knife in order to control the height of the transplants being excised.

3. A surgical instrument as claimed in claim 2, comprising: a sleeve carrying said limit flange and set on said shaft, longitudinally movable and rotatable thereon; a lug on said sleeve; said shaft being formed with several mutually spaced annular grooves each adapted for engagement with the aforementioned lug for determining the position of said sleeve.

4. A surgical instrument as claimed in claim 1, in which an elongated handle is secured on a proximal end of said hollow elongated cylindrical body extending transversely thereto, said securing device, securing the shaft relative to the body, being so situated as to secure, when in the secured position, the position of said knife, fastened on the shaft, and said handle, fastened on the body, in the same longitudinal plane.

5. A surgical instrument as claimed in claim 2, in which an elongated handle is secured on a proximal end of said hollow elongated cylindrical body transversely thereto, said device for securing the shaft relative to the body being so situated as to secure, when in the secured position, the position of said knife, fastened on the shaft, and said handle, fastened on the body, in the same longitudinal plane.

6. A surgical instrument as claimed in claim 1, in which said hollow cylindrical cutter is detachably secured to said hollow elongated cylindrical body.

7. A surgical instrument as claimed in claim 1, in which said knife is detachably secured to said shaft.

* * * * *